United States Patent [19]

Belykh et al.

[11] Patent Number: 5,201,771
[45] Date of Patent: Apr. 13, 1993

[54] ENDOPROSTHESIS OF THE HIP JOINT

[76] Inventors: Sergei I. Belykh, tovsky pereulok, 4, kv.66; Anatoly B. Davydov, Krasny Kazanets, 19, korpus 1, kv.283, both of, Moscow; Algimantas Y. Petrulis, pekt Krasnoi Armii, 122, kv.12; Sigitas V. Prantskyavichus, Myaures, 39, kv.13, both of, Kaunas, all of U.S.S.R.

[21] Appl. No.: 700,181

[22] PCT Filed: Sep. 15, 1989

[86] PCT No.: PCT/SU89/00243
§ 371 Date: May 22, 1991
§ 102(e) Date: May 22, 1991

[87] PCT Pub. No.: WO91/03991
PCT Pub. Date: Apr. 4, 1991

[51] Int. Cl.[5] .......................... A61F 2/36; A61F 2/32
[52] U.S. Cl. ........................................ 623/23; 623/22
[58] Field of Search ..................... 623/18, 16, 22, 23

[56] References Cited

U.S. PATENT DOCUMENTS

| 4,153,953 | 5/1979 | Grobbelar | 623/23 |
| 4,347,234 | 8/1982 | Wahlig et al. | 623/16 X |
| 4,718,915 | 1/1988 | Epinette | 623/23 |
| 4,990,161 | 2/1991 | Kampner | 623/16 |

Primary Examiner—David J. Isabella
Assistant Examiner—Dinh X. Nguyen
Attorney, Agent, or Firm—Burgess, Ryan & Wayne

[57] ABSTRACT

An endoprosthesis of the hip joint, comprising a head (1) insertable into the cotyloid cavity, and a pin (2) insertable into the medullary canal of the femoral bone. The pin (2) has in its top portion a through hole (3) for a U-clamp (4) to pass through, which U-clamp is secured in the hole (3) by means of a stud (5), both of the abovementioned U-clamp and stud being made of a biologically destructible polymer material. The middle portion of the pin (2) has at least two longitudinal slots (6), wherein combined movable inserts (7) are fitted, while the portion of the inserts that adjoins the bone surface is made of a biologically destructible polymer material. The bottom portion of the pin (2) is provided with a cap (8) made of a biologically indifferent polymer material.

7 Claims, 4 Drawing Sheets

ENDOPROSTHESIS OF THE HIP JOINT

FIELD OF THE INVENTION

The present invention relates generally to medicine and more specifically to endoprostheses of the hip joint made use of in traumatology and orthopedics, and enables one to effect prosthetic restoration of the femoral head without preliminary enlargement of the medullary canal, as well as to fix the head of the hip joint prosthesis with the aid of additional construction elements made of polymer materials, thus avoiding subsequent resorption of osseous tissue and adding much to the life time of the hip joint endoprosthesis.

BACKGROUND OF THE INVENTION

Known in the art is the prosthetic hip joint Gilibertya P. shaped as a metallic pin inserted into the medullary canal of the femur, a metallic spherical head connected to the pin and introduced into the cotyloid cavity, and a cup-shaped metallic sphere insertable into the cotyloid cavity, i.e., such a sphere that is in contact with the head of the prosthetic hip joint in the course of its functioning (U.S. Pat. No. 3,982,281).

In such an endoprosthesis its pin has a cross-sectional area, which gradually diminishes towards the pin bottom end so that the maximum pin width is less than the diameter of the medullary canal throughout the entire pin length. That is why such a hip joint prosthesis is installed with the aid of additional fixing. Such fixation is carried out with the use of curable osseous cements. To this end after having removed, for a required depth, the spongy layer and the bone marrow, a liquid non-cured composition of osseous cement is injected into the thus-formed hollow space, whereupon the pin of an endoprosthesis is inserted into said space.

However, such a construction of the endoprosthesis under consideration fails to provide its reliable fixing in the medullary canal, which is due to low adhesion between the skin surface and the osseous cement, as well as to a wide difference between the elasticity modulus of the material of the endoprosthesis pin and that of the osseous cement and the femoral bone itself.

All the above-stated results, under permanent cyclic load, in loosening of the endoprosthesis and resorption of the bone surfaces. According to recent evidence, 80 percent of such endoprostheses are to be removed after 5 to 7 years of functioning.

Known in the art is the endoprosthesis Niederer (U.S. Pat. No. 4,430,76) which is also shaped as a metallic pin adapted to be introduced into the femoral medullary canal, and a head insertable into the cotyloid cavity. The pin of the prosthesis in question is made as two components arranged at an angle to each other whose plain flat surfaces are provided with a plurality of shallow additional parallel grooves arranged lengthwise of the pin. Such an endoprosthesis is also installed with the use of osseous cements, so that said grooves are filled with the cement. Provision of such grooves adds to the adhesion between the cement and the pin and makes fixation of the prosthesis more reliable. However, even with such construction of the endoprosthesis too great a difference between the elasticity moduli of the cement and pin and permanent cyclic load applied to the hip joint endoprosthesis result in loosening of the latter in the medullary canal, so that the percentage of the prosthesis removed in 5 to 7 years is the same as in the endoprosthesis construction discussed hereinabove.

Known in the present state of the art is an artificial hip joint of the Sivash system, incorporating a metallic cotyloid cavity and an articulated device aimed at substitution of the femoral head. The pin of the endoprosthesis is fashioned as a shaped solid metallic rod, which is tightly inserted into the preliminarily enlarged medullary canal without any additional fixing (cf. 'Operative orthopedics' by Movshovich, 1983, Meditsina Publishers, Moscow, pp. 203–207 (in Russian)).

Installation of the aforementioned endoprosthesis should necessarily be preceded by enlargement (by drilling-out) of the medullary canal so as to provide exact correspondence of the latter to the diameter of the rod of the prosthetic joint, which inflicts additional operative injury on the patient operated upon. It is due to tight fixing of the endoprosthesis that its pin exerts permanent impact on the surface of the bone tissue, thus causing resorption of the latter and loosening of the endoprosthesis.

One more prior-art construction of an artificial hip joint is known to comprise a pin insertable into the bone marrow of the femur and a head to be introduced in the cotyloid cavity (cf. 'Operative orthopedics' by I. A. Movshovich, 1983, Meditsina Publishers, Moscow, pp. 216–217 (in Russian). When applied the pin of the prosthesis is tightly introduced into the preliminarily enlarged medullary canal and is additionally fixed with the aid of osseous cement. However, use of the prostheses of the character set forth hereinabove results in resorption of the bone tissue at the place of its contact with the metal of the pin. Employment of osseous cement to some extent diminishes such an adverse effect due to a more uniform load distribution over the bone surface.

However, such a redistribution results in some cases in that resorption of the bone tissue occurs in other places not contacting the pin, first and foremost, in the top and bottom portions of the femur which eventually results in loosening of the prosthesis. Moreover, use of osseous cement adds to labor consumption and duration of the operative procedure, as well as renders it impossible to regenerate the bone tissue at the place of application of said cement that is, makes it impossible for the pin of the endoprosthesis to accrete with its own bone tissue.

SUMMARY OF THE INVENTION

It is an object of the present invention to provide such an endoprosthesis of the hip joint that would make it possible, due to an appropriate material of which are made its construction elements, their arrangement and shape, to rule out subsequent resorption of the bone tissue and to add much to the effective service life of the endoprosthesis involved.

Said object is accomplished by an endoprosthesis of the hip joint, comprising a head insertable into the cotyloid cavity, and a pin insertable into the femoral medullary canal, according to the invention, the pin is provided with a through hole in its top portion, said hole being adapted for at least one U-shaped clamp to pass through, said clamp being made of a biologically destructible polymer material and being fixed in said hole by means of a stud made of a biologically destructible polymer material and fitted thrustwise between the U-clamp and the pin, the middle portion of the pin has at least two longitudinal slots, which accommodate composite movable inserts, one portion of each of said inserts adjoining the prosthesis pin being made of a biologically indifferent or destructible polymer material, while the other portion of each of the insert adjoining the bone surface, is made of a biologically destructible polymer material, and the bottom portion of the pin is provided with a cap made of a biologically indifferent polymer material.

Such a construction arrangement of the proposed endoprosthesis makes it possible to effect prosthetic restoration of the femoral head without preliminary enlargement of the medullary canal, as well as to fix the head with the aid of additional construction elements made of polymer materials, which rules out subsequent resorption of the bone tissue and adds much to the effective service life of the proposed endoprosthesis of the hip joint.

It is desirable that the lenth of the longitudinal slot be from 0.7 to 0.9 of the length of prosthesis pin, since a longer length of said slot will prevent the cap from being fitted in the prosthesis bottom portion, while with its length shorter than 0.7 of the pin length, mobility of the insert in the prosthesis bottom portion will be restricted, which complicates and affects adversely the holding of the prosthesis in the medullary canal.

It is expedient that the length of the movable insert be from 0.3 to 0.6 of the length of the endoprosthesis pin, since a shorter insert length might fail to provide an adequate insert fastening surface and hence stable prosthesis fixation, whereas a longer insert length might lead to that a portion of the insert will project beyond the limits of the longitudinal slot, which will necessitate removal of that projecting insert portion.

It is favorable that the portion of the insert which adjoins the prosthesis pin, would suit, as to its configuration, the profile of the longitudinal slot, while its portion adjoining the face of the medullary canal be shaped as a cylinder or a cone.

Such a construction feature will facilitate introduction of the inserts into the medullary canal and provide for the maximum possible contact area between the insert and the bone surface.

It is reasonable that the U-clamp insertable into the through hole of the pin, be made of a biologically indifferent polymer material, which enables the bone tissue to form in the space not occupied by the clamp and provides relaxation of stresses resulting from cyclic load that are liable to arise just after fitting the endoprosthesis in position.

The stud holding the U-clamp in place may be made of a biologically destructible polymer material featuring a period of biological destruction over two months, which provides a possibility for the patient's own bone tissue to grow into the through hole in the top portion of the prosthesis. The minimum required service life of the stud exceeds two months, which defines the destruction period of the material the stud is made of.

It is advantageous that the movable inserts, the stud, and the clamp, everything taken together or individually, would comprise physiologically potent medicinal substances or mixtrures thereof, which enables one to rule out postoperative complications and to establish most favourable conditions for regeneration of the bone tissue, which provides for prolonged functioning of the endoprosthesis proposed herein.

BRIEF DESCRIPTION OF THE DRAWINGS

In what follows the invention will be disclosed in a detailed description of specific exemplary embodiments thereof given by way of illustration with reference to the accompanying drawings, wherein.

DETAILED DESCRIPTION OF THE INVENTION

Figure 1:
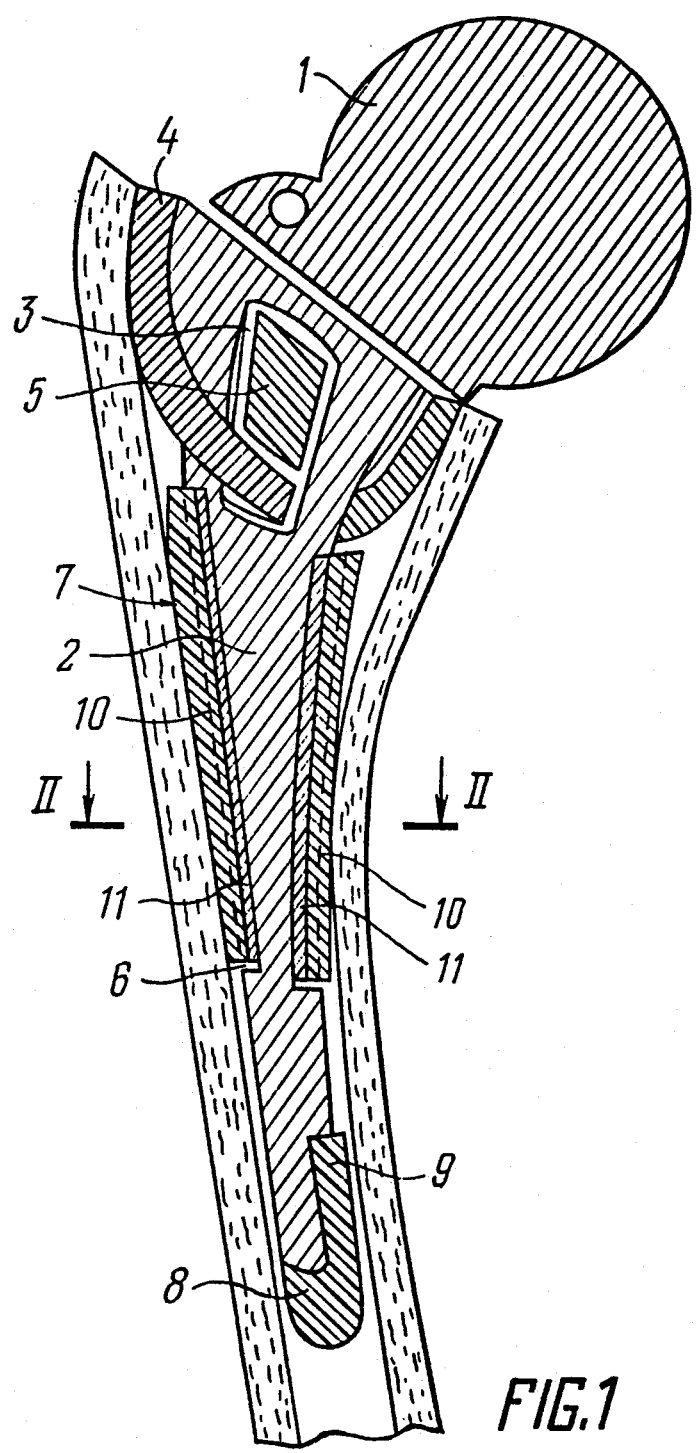
FIG. 1 is schematic front sectional view of the endoprosthesis of the hip joint, according to the invention.

The proposed endoprosthesis of the hip joint comprises a head 1 and a pin 2 (FIG. 1) whose top portion has a through hole 3, which is adapted for a U-clamp 4 to pass through, said U-clamp being made of a polymer material and being fixed in said hole with the aid of a stud 5 made also of a polymer material. The middle portion of the pin 2 has longitudinal slots 6 (FIGS. 2, 3), which accommodate movable inserts 7 made of a polymer material. The bottom portion of the pin 2 (FIG. 1) is provided with a cap 8 also made of a polymer material and featuring a projection 9.

Figure 2:
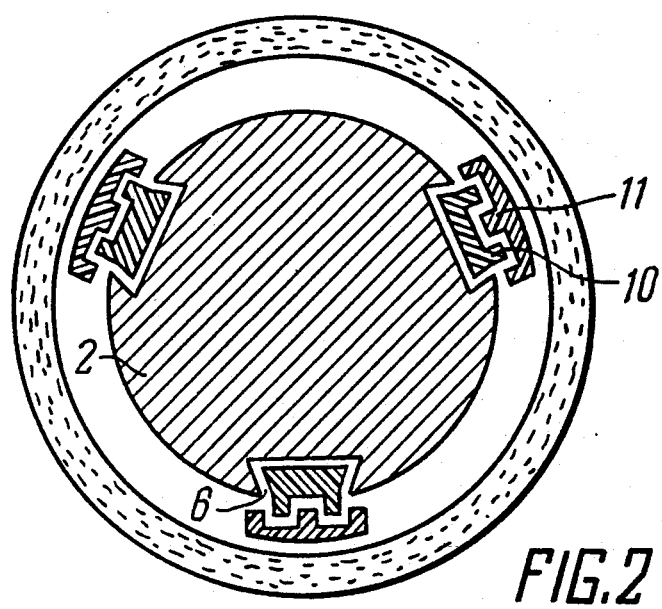
FIG. 2 is a sectional view taken along the line II—II in FIG. 1.
Figure 3:
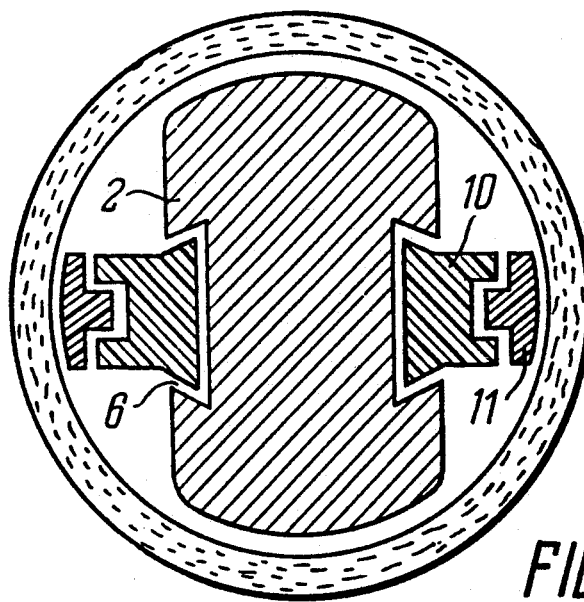
FIG. 3 is a sectional view similar to FIG. 2 of another embodiment of the arrangement of the inserts in the pin of the prosthesis, according to the invention.
Figure 4:
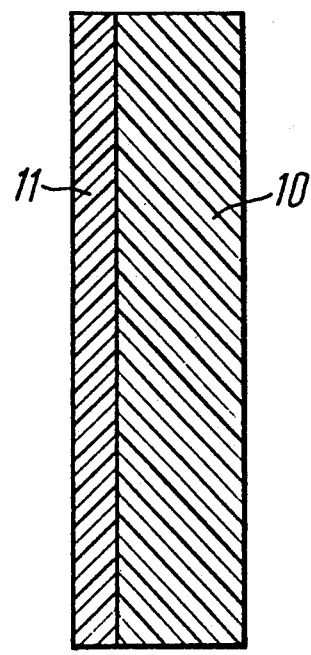
FIG. 4 is a longitudinal sectional view of an insert featuring cylindrical configuration of its portion adjoining the face of the medullary canal, according to the invention.
Figure 5:
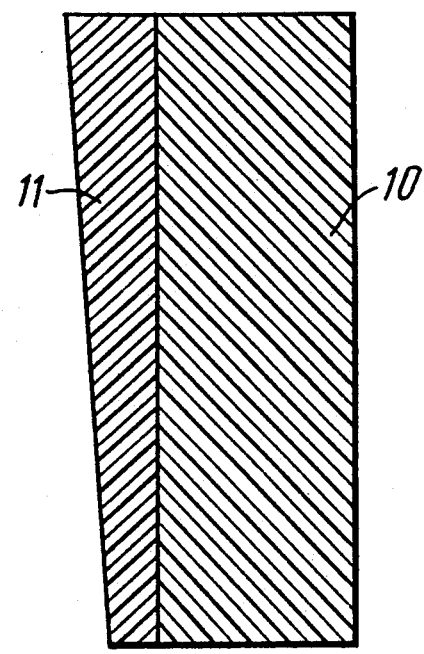
FIG. 5 is a longitudinal sectional view of an insert featuring cone shaped configuration of its portion adjoining the face of the medullary canal, according to the invention.
Figure 6:
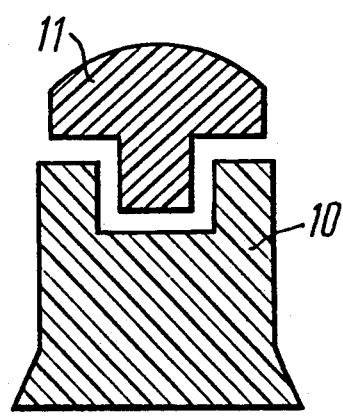
FIG. 6 is a cross-sectional view of one of the embodiments of the insert.
Figure 7:
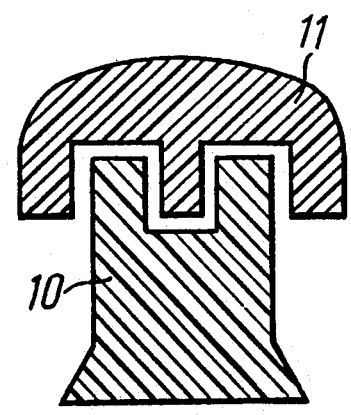
FIG. 7 is a cross-sectional view of another embodiment of the insert.

The combined movable insert 7 is comprised of two portions 10 and 11 (FIGS. 1, 2, 3). The portion 10 (the inner one) engageable in the longitudinal slot 6 of the pin 2, suits the shape of the slot 6 and is made of a biocompatible or slowly resorbing polymer material, while the portion 11 (the outer one) adjoining the face of the medullary canal, is made of a resorbable polymer material and may have either cylindrical or conical configuration (FIGS. 4, 5, 6, 7).

Two-component design of the insert 7 made up of the portions 10 and 11 is concerned with the specific functional features of the initial fixation and operation of the prosthesis involved. The presence of an outer readily resorbable layer in the insert 7 provides for a reliable fixing of the prosthesis at the first stage of its installation and, after resorption, makes possible regeneration of the bone tissue at the same place, which ensures thickening of the bone and hence reliable fixing and prolonged functioning of the endoprosthesis. The inner portion 10 of the insert 7 made of a biocompatible or slowly resorbable composite elastic material plays the part of a damper, after the prosthesis has accreted with its own bone tissue, said damper being aimed at a uniform destribution of permanently arising nonuniform cyclic loads, thus ruling out resorption of the bone tissue, which occurs when the latter gets in a direct contact with the metallic pin 2 of the prosthesis.

The longitudinal slot 6 provided in the middle portion of the pin 2 equals from 0.7 to 0.9 the whole length of the pin 2, while the movable insert 7 accommodated in the longitudinal slot 6, is equal to 0.3 or 0.6 the entire pin length.

The U-clamp 4 passing through the open-end hole 3, and the stud 5 securing the U-clamp therein, are made of a resorbable polymer material having a resorption period of at least two months. The length of the stud 5 should be less than or equal to the diameter of the medullary canal, while the cross-section diameter or thickness of the U-clamp 4 should be less than or equal to a distance between the pin 2 of the endoprosthesis and the bone surface.

It is advantageous that the cap 8 provided in the bottom portion of the prosthesis, be made of a biocompatible polymer material, which is necessary to preclude the contact between the bottom portion of the prosthesis pin 2 and the bone tissue and to provide lower stresses at the place of contact.

The proposed endoprosthesis of the hip joint is applied as follows.

An incision is made of the soft tissues in the region of the hip joint, whereupon the pathologically changed head and neck of the femoral bone are ablated. Then the pin 2 of the endoprosthesis is selected that its size be somewhat less than the diameter of the medullary canal in its narrowest portion. Next the movable inserts 7 are fitted in the longitudinal slots 6 and the U-clamp 4 is fixed in the through hole 3 with the aid of the stud 5, whereupon the pin 2 of the endoprosthesis is inserted into the medullary canal as deep as necessary. Insertion of the pin 2 causes the ends of the U-clamp 4 to bring together with the result that said ends get in contact with the bone surface in the greater intertrochanteric space. Then the movable inserts 7 are buried distally, with the aid of an impactor as far as they become jammed rigidly between the inner cortical layer and the pin of the endoprosthesis. The portions of the clamp 4 that protrude beyond the limits of the medullary canal are to be cut off, the head 1 of the endoprosthesis is inserted into the cotyloid cavity, and the operative wound is stitched up in layers.

Figure 8:
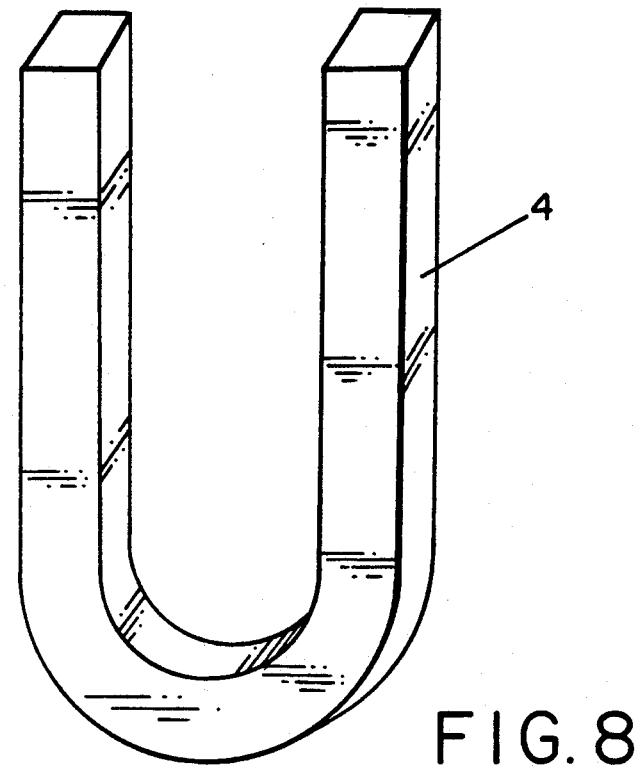
FIG. 8 is a view in perspective of a U-clamp having a rectangular cross section.

FIG. 8 shows an embodiment in perspective of a U-clamp (4) with a rectangular cross-section as shown in the examples. The U-clamp can also have other cross-sections such as circular.

Figure 9:
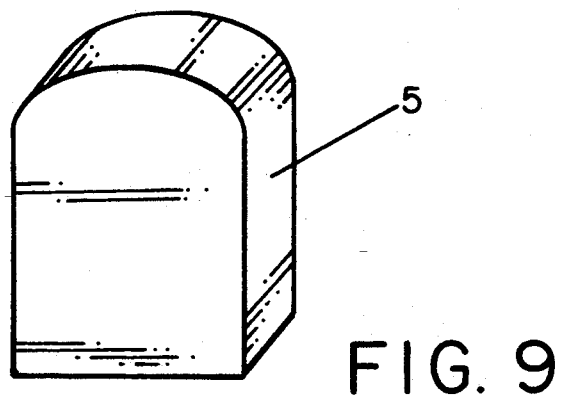
FIG. 9 is a partial view in perspective of an embodiment of the stud.

FIG. 9 shows a partial perspective view of an embodiment of a stud (5) for holding the U-clamp in the through hole.

To promote understanding of the present invention, given below are some specific examples of its practical application.

EXAMPLE 1

The case involves pseudarthrosis of the femoral neck, aseptic necrosis of the femoral head, secondary coxarthrosis. The hip joint is cut open under general anesthesia, and the deformed femoral head is ablated without enlarging the femoral medullary canal. Then the pin 2 of the endoprosthesis (Poldie-Czech's, cf. 'Operative orthopedics' by I. L. Movshovich, 1983, Meditsina Publishers, Moscow) is inserted into the proximal end of the femoral bone, said pin 2 having a cross-section of 11×5 mm and a length of 125 mm and being provided with two trapezoidal longitudinal slots 8 mm wide and 110 mm long. Two movable shaped inserts 7 (75 mm long) are fixed in place in said longitudinal slots 6, the inner portion 10 of said inserts being made of medical polydodecaneamide, while the outer portion 11 thereof is made of a copolymer of N-vinylpyrrolidone with methylmethacrylate reinforced with kapron fibre.

A film of a copolymer of N-vinylpyrrolidone with methylmethacrylate, incorporating 20 percent of the anti-microbial drug dioxidin of gentamycin. The through hole 3 (which appears as a shaped recess in this particular case) provided in the top portion 2, accommodates the U-clamp 4, which is fixed in place therein with the aid of the stud 5, said clamp 4 being made of a copolymer of N-vinylpyrrolidone with methylmethacrylate reinforced with kapron fibre and comprising on its surface not in touch with the bone surface or with the endoprosthesis pin 2, a polymer coating made of a mixture of a copolymer of N-vinylpyrrolidone with butylmethacrylate, and gentamycin, while the stud 5 is made of a composition made up of ethylcyanacrylate in a mixture with calcium gluconate, orotic acid and dioxidin. The clamp 4 features a width which is equal to the width of the endoprosthesis pin 2, a thickness of 2 mm, and a length of 60 mm.

The pin 2 is provided with the shaped cap 8 at its end, said cap being made of polydodecaneamide, while its outer surface is coated with a film of a copolymer of N-vinylpyrrolidone with methylmethacrylate, said copolymer incorporating also a mixture of calcium gluconate with gentamycin.

Next the pin 2 is inserted into the medullary canal whose narrowest portion is 13 mm wide and the movable inserts 7 are introduced until they get jammed. When introduced the clamp 4 is compressed and enters, together with the pin 2, into the medullary canal, until they get in contact with the faces of said canal. Then the portions of the clamp 4 extending for 15 mm are cut off with the aid of nippers, whereupon the operative wound is stitched up in layer without applying any additional immobilization. In two weeks the hip joint operated upon is subjected to partial loading, while complete loading is applied to the hip joint after a three-month period. Status on control examination after one year: consolidation of the bone tissue at the place of insertion of the slidable inserts 7; appearing of spongy bone tissue in the expanding portion at the place of location of the clamp 4. Status on follow-up observation in a three-year period: the functions of the hip joint restored completely. X-ray findings: no resorption of the bone tissue whatever.

EXAMPLE 2

The case involves traumatic deforming arthrosis of the hip joint. The hip joint is cut open, the deformed femoral head is ablated, wherupon the pin 2 of the endoprosthesis (Ring's) having a cross-section of 11×5 mm and a length of 90 mm, is inserted into the proximal end of the femoral medullary canal whose narrowest portion in 14 mm wide. The pin 2 has the longitudinal shaped slots 7 mm wide and 75 mm long, wherein the movable inserts 7 (40 mm long) are fixed in place. The inner portion 10 of the inserts 7 is made of a copolymer of N-vinylpyrrolidone with methylmethacrylate (nitrogen content 1.4 wt %) reinforced with laysan fibre, while the outer portion 11 thereof is made of a copolymer of N-vinylpyrrolidone with methylmethacrylate reinforced with acid-treated kapron fibre.

The inner surface of the insert 7 is coated with a film made of the same copolymer incorporating 15 percent of carbenicillin and 10 percent of potassium orotate.

The U-clamp 4 having a diameter of 2.5 mm and made of a copolymer of N-vinylpyrrolidone with butylmethacrylate, containing 30 percent of calcium gluconate in a mixture with polyalkylcyanacrylate reinforced with kapron fibre, is fixed in a shaped recess in the top portion of the pin 2 with the aid of the stud 5 made of the same copolymer and having a thickness of 11 mm. The tongues of the clamp are 50 mm long and are spaced 18 mm apart in the top portion. The end of the pin 2 mounts the cap 8 (12 mm long), made of a copolymer of N-vinylpyrrolidone with methylmethacrylate (nitrogen content 1.4 mt %) and having a shaped recess in its top portion where the longitudinal slots 6 runs. The pin 2 with the inserts 7 held thereto in its top portion is inserted into the medullary canal as deep as necessary so that the clamp tongues also enter into the medullary canal until contacting with the face of the canal in its widened portion. Then the inserts 7 are introduced until getting jammed so as to fix the endoprosthesis in place. In this case the endoprosthesis end protected by the cap 8 is also brought in contact with the bone surface. Next the operative wound is stitched up in layers and heals by first intention. The limb operated upon is subjected to partial loading in two weeks after surgery, while complete loading is applied in 96 day after surgery. Evidence of one-year after-examination: the implanted endoprosthesis in a stable position. X-ray findings: no bone resorption whatever, bone thickened at the place of introduction of the inserts and the tongues of the clamp 4.

EXAMPLE 3

The case is one of aseptic necrosis of the femoral head. The hip joint is cut open, the necrotized femoral head is ablated. The pin 2 of the endoprosthesis (Movshovich's) 9 mm in diameter and 90 mm long, is introduced into the proximal end of the femoral medullary canal whose narrowest portion is 13 mm wide, said pin having three trapezoidal longitudinal slots 6.6 mm wide and 63 mm long. The slots 6 accommodate the movable inserts 7, which are held in place therein and feature a length of 28 mm, while their extending portion is 2 to 2.5 mm long. The inner portion 10 of the inserts 7 is made of polypropylene, while the outer portion 11, of a copolymer of N-vinylpyrrolidone with methylmethacrylate reinforced with oxycellulose fibre. The clamp having a square cross-sectional area of 4 cm$^2$ is fixed in a through recess provided in the top portion of the pin 2 with the aid of the stud 5 13 mm thick, said clamp 4 being made of a copolymer of N-vinylpyrrolidone with butylmethacrylate reinforced with kapron fibre, while said stud 5 is made of a mixture of cyanacrylate with bone chips. The tongues of the clamp are 40 mm long and are spaced 16 mm apart in the top portion. The end of the pin 2 mounts the cap 8 14 mm long made of polydodecaneamide and having a shaped recess 8 mm long in its top portion. Then the pin 2 with the inserts 7 temporarily fixed in the upper position, are introduced into the medullary canal as deep as necessary, with the result that the tongues of the clamp 4 enter into the expanded canal portion as far as to get in obligatory contact with the canal inner face. Next the inserts 7 are introduced into the medullary canal, thus fixing the endoprosthesis in position by virtue of jamming. Finally, the operative wound is stitched up in layers and heals by first intention. The limb operated upon undergoes partial loading in 12 days after surgery, while complete loading is applied to the limb in 64 days after surgery. Control after-examination carried out 27 months after surgery: the implanted endoprosthesis in a stable position; no resorption whatever of the bone tissue; consolidated bone tissue over the entire surface of the endoprosthesis.

EXAMPLE 4

The case is one of necrosis of the femoral head. The hip joint is cut open, the necrotized femoral head is ablated. The pin 2 of the endoprosthesis (Movshovich's) 8 mm in diameter and 85 mm long, is introduced into the proximal end of the femoral medullary canal whose narrowest portion is 12 mm wide, said pin having three trapezoidal longitudinal slots 6, 5 mm wide and 58 mm long. The movable inserts 7, 27 mm long and having their extending portion 1.9 to 2.2 mm long, are secured in the slots 6. The inner portion 10 of the inserts 7 is made of a copolymer of N-vinylpyrrolodone with methylmethacrylate (nitrogen content 1.2 wt %), while the outer portion 11 is made of the same copolymer reinforced with acid-treated kapron fibre. The inner surface of the inserts 7 is provided with a coating of the same copolymer, containing a mixture of gentamycin and potassium orotate. The clamp of a round cross-section having a diameter of 2.2 mm is held in a through recess provided in the pin top portion with the aid of the stud, said clamp being made of a copolymer of N-vinyleyrrolidone with methylmethacrylate reinforced with kapron fibre, while said stud is made of a polyethylcyanacrylate, containing a mixture of calcium gluconate, orotic acid, and dioxidin. The cap 8 is made fast at the pin end, said cap having a 6-mm long inner recess. The endoprosthesis is implanted and fixed in place as described in Example 3.

The limb operated upon undergoes partial loading in 14 days after surgery, while complete loading occurs in 78 days after surgery. Evidence of follow-up observation after 32 months: endoprosthesis in a stable position; no bone resorption whatever; bone thickening in the place of introduction of the inserts 7 and in the top portion of the femur.

Industrial Applicability

The proposed endoprosthesis of the hip joint enables one to effect prosthetic restoration of the femoral head without preliminary enlargement of the medullary canal, provides for reliable fixing of the implanted prosthesis, reduces the amount of postoperative complications, and prolongs the prosthesis service life.

What is claimed is:

1. An endoprosthesis for a hip joint, for surgical implantation in a cotyloid cavity and a medullary canal of a femoral bone, comprising
    a femoral element having a head to be inserted into the cotyloid cavity;
    a shaft having a predetermined length and upper, middle and lower portions to be inserted into the medullary canal, said upper portion of said shaft has a through hole and said middle portion of said shaft has two longitudinal slots having a length less than said length of said shaft;
    at least one U-clamp and a stud formed of resorbable material;
    inserts having a first part and a second part, said first and second part being made of a resorbable material wherein said second part has a faster rate of resorbtion than said first part, said inserts being movably mounted in said slots such that said first part is adjacent to the shaft and said second part is adjacent to the bone;

an end cap configured to be disposed over the lower portion of said shaft;

wherein said U-clamp is configured to pass through said through hole and said stud is shaped to fit in said through hole adjacent said U-clamp thereby stabilizing said U-clamp with respect to the shaft.

2. An endoprosthesis for the hip joint of claim 1, wherein the length of the longitudinal slots equals 0.7 to 0.9 the length of the shaft.

3. An endoprosthesis for the hip joint of claim 1, wherein the length of the inserts equals 0.3 to 0.6 the length of the shaft.

4. An endoprosthesis for the hip joint in claim 1, wherein the configuration of the first part of the insert corresponds to the longitudinal slot, and the second part of the insert has a shape of a cylinder or a cone.

5. An endoprosthesis for the hip joint of claim 1, wherein the U-clamp comprises a biocompatible polymer material.

6. An endoprosthesis for the hip joint of claim 1, wherein the stud comprises a resorbable polymer material with a period of resorbtion exceeding two months.

7. An endoprosthesis for the hip joint of claim 4, wherein the movable inserts, the stud, and the U-clamp comprise physiologically potent medicinal substances.

* * * * *